United States Patent
Lai

(10) Patent No.: US 11,617,718 B2
(45) Date of Patent: *Apr. 4, 2023

(54) PROCESS FOR PRODUCING A NANO-CBD MICROEMULSION SYSTEM

(71) Applicant: Hai Nam Lai, Ho Chi Minh (VN)

(72) Inventor: Hai Nam Lai, Ho Chi Minh (VN)

(*) Notice: Subject to any disclaimer, the term of this patent is extended or adjusted under 35 U.S.C. 154(b) by 358 days.

This patent is subject to a terminal disclaimer.

(21) Appl. No.: 16/537,596

(22) Filed: Aug. 11, 2019

(65) Prior Publication Data

US 2019/0365647 A1    Dec. 5, 2019

(51) Int. Cl.

| | | |
|---|---|---|
| *A61K 8/42* | (2006.01) | |
| *A61K 31/164* | (2006.01) | |
| *A61K 31/165* | (2006.01) | |
| *A61K 31/404* | (2006.01) | |
| *A61K 31/4164* | (2006.01) | |
| *A61K 9/70* | (2006.01) | |
| *A61K 8/49* | (2006.01) | |
| *A61K 9/06* | (2006.01) | |
| *A61Q 19/00* | (2006.01) | |
| *A61K 8/02* | (2006.01) | |
| *A61P 17/00* | (2006.01) | |
| *A61K 8/44* | (2006.01) | |
| *A61Q 19/08* | (2006.01) | |
| *A61K 9/107* | (2006.01) | |
| *A61K 47/10* | (2017.01) | |
| *A61K 31/05* | (2006.01) | |

(52) U.S. Cl.
CPC ............ *A61K 9/1075* (2013.01); *A61K 31/05* (2013.01); *A61K 47/10* (2013.01)

(58) Field of Classification Search
None
See application file for complete search history.

(56) References Cited

FOREIGN PATENT DOCUMENTS

CN        103110582 A   *   5/2013

* cited by examiner

*Primary Examiner* — Layla Soroush
(74) *Attorney, Agent, or Firm* — BN IP-Consulting LLC; Binh-An Nguyen

(57) ABSTRACT

The present invention relates to a process of producing a nano-CBD microemulsion system includes: (i) preparing a dispersal phase by dissolving CBD in an ethanol solvent in a ratio between mass of CBD:volumn of ethanol solvent as 8:10 at a speed of 300 to 500 rpm with heating to a temperature ranging from 40 to 60° C. within 4 to 8 hours; (ii) preparing a carrier by heating a liquid PEG (polyethylene glycol) accounted for 40-60% by mass of the mixture of PEG and water to a temperature from 60 to 80° C., stirring homogeneously; (iii) adding the carrier to the dispersal phase in a ratio by mass of 40:60, continuing heating the dispersal phase to a temperature of 40 to 60° C., stirring at a speed of 400 to 800 rpm; (iv) elmusifying as follows: when the temperature arrives at 100° C., adding ACRYSOL K-140 to the mixture of the carrier and dispersal phase obtained in step (iii) in a ratio by mass of 40:60, continuing to stir at a speed of 500 to 700 rpm, at a temperature of about 100° C., in vacuum, the reaction temperature is kept at 100° C. for 3 to 5 hours, controlling the quality of resulting products until it is transparent, the reaction is quenched, the temperature is decreased slowly until it is in the range of 40 to 60° C.; emulsifing the entire mixture for 30 minutes, at a speed of 400 to 800 rpm. (v) filtrating the products by injecting through nanofilters before filling-packaging.

1 Claim, 1 Drawing Sheet

PROCESS FOR PRODUCING A NANO-CBD MICROEMULSION SYSTEM

TECHNICAL FIELD

The present invention relates to a process for producing a nano-CBD microemulsion system.

BACKGROUND OF THE PRESENT INVENTION

Cannabidiol (CBD) is a cannabinoid which is a cyclohexene substituted by a methyl group at position 1, a 2,6-dihydroxy-4-pentylphenyl group at position 3 and a prop-1-en-2-yl group at position 4. It acts as a plant metabolite. Cannabidiol, a phytocannabinoid derived from Cannabis species, does not have psychophysiological activity and is applied in pain-alleviation, anti-inflammation, anti-cancer and used in chemotherapies.

CBD is represented by chemical formula $C_{21}H_{30}O_2$, which has the molecular weight of 314.469 g/mol and the molecular structure as follows:

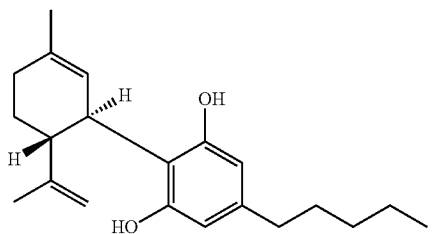 [SMILES: C=C(C)[C@@H]1CCC(C)=C[C@H]1c1c(O)cc(CCCCC)cc1O]

When being used, cannabidiol (CBD) has actions against the proliferation, the angiogenesis and pro-apoptotic via various mechanisms, it may not relate to the signaling by cannabinoid receptors 1 (CB 1), CB2 or vanilloid receptors and inhibits AKT/mTOR signals, therefore activates the autophagy—a process in which a cell "eats" the components of its own, which is a basically catabolic mechanism, related to the degration of unnecessary components or dysfunctioned components in the cell, via the actions of lysosomes and promotes the apoptosis—a process of programed cell deaths. Additionally, CBD enhances the generation of reactive oxygen species (ROS), which helps to further enhance the apotosis. This agent also upregulates the expression of molecules adhered among cells 1 (ICAM-1) and issue inhibitors of matrix metalloproteinase-1 (TIMP1) and reduces the expresion of DNA binding inhibitors 1 (ID-1). This inhibits the invasion of cancer and metastatic cells. CBD can also activate transiently potential vanilloids type 2 (TRPV2), which can increase the absorption of various cytotoxic agents in cancer cells. CBD has been demonstrated to have effects on pain-alleviation, anti-convultion, muscle stretching, anxiety-reduction, anti-oxidation, and anti-hysteria-epilepsy. These diverse effects may be due to the complex pharmacological mechanism of CBD. In addition to the constraint of CB1 and CB2 receptors of endocannabinoid systems, there is an evidence that CBD activates serotonines 5-HT1A and vanilloid receptors TRPV1-2, alpha-1 adrenergic antagonists and μ-opioid receptors, inhibits the synaptosomal absorption of noradrenalines, dopamines, serotonines and gaminobutyric acids and the cell absorption of anandamids, acts on Ca2 shops of mitochondrions, blocks low voltage-activated Ca2 channels (type T), stimulates the action of inhibitory glycine-receptors and inhibits the action of aliphatic hydrolases (FAAH).

CBD has high activity in the body but low bioavailability, according to the study by Mechoulam R et al., published on Journal of Clinical Pharmacology, the bioavailability when being used orally is only 13-19%, while being used nasally (inhalantly) is about 31%. It is fastly metabolised and the half-life is within about 9 hours. CBD is well-absorbed after administered orally, and has high activity in the body but low bioavailability. Thus, it is very necessary to improve the ability of absorption, increase the bioavailability of the agent. Applying nano technologies is a novel technological application for generating vehicle systems and increasing the bioavailability of the agent. When particle sizes are below 100 nm, the ability of absorption and the ability of storage will increase. CBD packaged in nano-vehicle systems helps transport an agent to targets in a selectively, effectively and drug-saving way. In our country, nano technologies in biomedical fields remain new and not yet have many applications but have attracted so much interest to study. The most common existing studies are the applications of nanocurumin and drug transporting systems to target cells, there have not been studies to manufacture nano-CBDs. Using nanoparticles to carry and release drugs is a new strategy for treating diseases, particularly epilepsy and cancers in the future.

Anitha Krishnan Nair et al. in US Patent Publication No. 2011/0229532 A1 provided a process for producing a microemulsion system of compounds belonging to an oleophylic polyphenol group by using ultrasonic with non-ionic surfactants and one non-ionic solvent to enhance the water solubility. In particular, the invention relates to a nanoprocessing of curcumin and its derivates which is not applied for other agents.

Robert WINNICKI et al. in Patent publication No. WO2013009928A1 provided cannabinoid formula. One kind of solution micelle suspensions of one or more cannabinoid analogues creates particles with dimensions of 50 to 1000 nm, another kind is a liposome formula of one or more cannabinoid analogues with particle sizes of 200 to 400 nm.

The mentioned-above processes provide micelles with dimensions greater than 100 nm, these particles do not have uniform dimensions then the water-soluble effectiveness is still not high. Processes for generating micelles of curcumin and its derivates can not be applied for CBD because those will lose the activity of CBD.

Therefore, there is a demand of a process for producing a microemulsion system having micelles with dimensions smaller than 100 nm, uniformity, better water-solubility while retaining the structure, activity of CBD in nanoprocessing.

SUMMARY OF THE PRESENT INVENTION

An object of the present invention is to provide a process for producing a nano-CBD microemulsion system that aims at overcoming disadvantages of the known mentioned-above processes to produce particles having dimensions smaller than 200 nm, uniformity, ability to dissolve in water while the activity and structure is retained to help increase utility effects of CBD active agents, in particular, increase the ability of absorption and increase the bioavailability.

To achieve the above object, the process for producing a nano-CBD microemulsion system of the present invention includes:

(i) preparing a dispersal phase by dissolving CBD in an ethanol solvent in a ratio between mass of CBD:volumn of ethanol solvent as 8:10 by a stirrer at a speed of 300 to 500 rpm with heating to a temperature from 40 to 60° C. within 4 to 8 hours;

(ii) preparing a carrier by heating a liquid PEG (polyethylene glycol) accounted for 40-60% by mass of the mixture of PEG and water to a temperature ranging from 60 to 80° C., stirring homogeneously;

(iii) adding the carrier to the dispersal phase in a ratio by mass of 40:60, continuing heating the said dispersal phase to a temperature ranging from 40 to 60° C., stirring at a speed of 400 to 800 rpm;

(iv) elmusifying as follows: when the temperature arrives at 100° C., adding ACRYSOL K-140 to the mixture of the carrier and dispersal phase in step (iii) in a ratio by mass of 40:60, continuing to stir at a speed of 500 to 700 rpm, at a temperature of about 100° C., in vacuum, the reaction temperature is kept at 100° C. for 3 to 5 hours, controlling the quality of resulting products by dissolving into water and measuring the transparency, if it fails then continuing heating and measuring this transparency every 30 minutes until it is observed to be transparent, the reation is quenched, the temperature is decreased slowly until it is in the range of 40 to 60° C.; emulsifying the entire mixture for 30 minutes, at a speed of 400 to 800 rpm.

(v) filtrating the products by injecting through nanofilters before filling-packaging.

DETAILED DESCRIPTION OF THE PRESENT INVENTION

Figure 1:
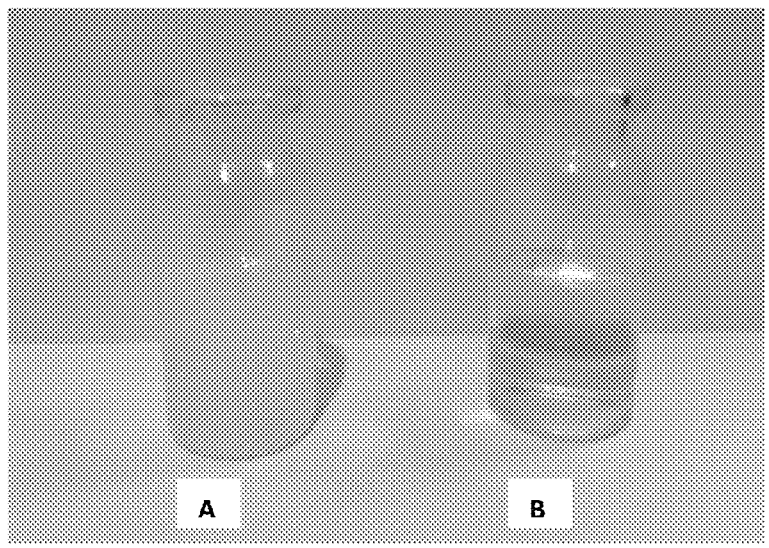
FIG. 1 shows a picture comparing the water-dispersing ability between a known 99% CBD and the nano-CBD obtained by the process of the invention.

The process for producing a nano-CBD microemulsion system of the present invention is performed as follows:

(i) First step: preparing a dispersal phase by dissolving CBD in an ethanol solvent in a ratio between mass of CBD:volumn of ethanol solvent as 8:10 by a stirrer at a speed of 300 to 500 rpm and simultaneously heating to a temperature of 40 to 60° C. within 4 to 8 hours. The inventors used ethanol as a solvent that is capable of dissolving CBD well, helps form a better dispersal phase and facilitate this dispersal phase being able to combine better with PEG carriers. Using hydroxyl (OH—) based-ethanol solvent forms a linkage with water then has effects on stablizing the structure of the oil-in-water microemulsion system. By experiments, the inventors determined that, in a 8:10 ratio of CBD:ethanol (mass:volumn), CBD achieved the highest solubility and avoided the redundance of ethanol solvent, which is a wastage. The use of stirring and heating generates CBD dispersing better, when the inventors carried out the experiments under various stirring conditions and temperatures, it was shown that at a speed of 300-500 rpm and simultaneously heating at a temperature ranging from 40 to 60° C., the dispersal phase of CBD was better and the combination with PEG carriers was better.

(ii) Second step: preparing a carrier by heating a liquid PEG (polyethylene glycol) accounted for 40-60% mass of the mixture of PEG and water to a temperature from 40 to 60° C., stirring homogeneously.

When being used, CBD is often damaged in the digestive tract, a portion is absorbed into the blood, most of the rest is eliminated. Thus, it needs a process for producing micelles containing CBD active agents that have small sizes with bio-coatings, stable structure, inadherence and high solubility. Because the microemulsion system of the present invention is employed in food and pharmaceutical industries, the agents selected to use must have high safety, non-toxicity and less side effects.

Many studies have shown that transporting processes of drugs may be improved the effectiveness by vehicle systems derived from kinds of polymers: natural hydrophilic polymers such as proteins (gelatine, albumine), polysaccharides (alginate, dextrane, chitosane), synthetic hydrophobic polymers such as polyesters (poly (ε-capprolactone), polylactic acids, polylactic-co-glycolic acids. Polymer carriers with relatively high drug loadings can confer many conveniences in pharmacokinetics, namely drugs are kept stably, which can be administered to treat for a long time by the slowly-released process of drugs according to the decomposition of polymers, the biological distribution of drugs, the targeting, the penetration through cell membranes, etc. that can be driven by physicochemical properties of polymers.

(iii) Third step: adding the carrier to the dispersal phase (in a ratio of 40:60), continuing heating the dispersal phase to 100° C., stirring at a speed of 400 to 800 rpm.

(iv) Forth step: elmusifying as follows: when the temperature arrives at 100° C., adding ACRYSOL K-140 to the mixture of the carrier and dispersal phase obtained in step (iii) in a ratio by mass of 40:60, continuing to stir at a speed of 500 to 700 rpm, at a temperature 50-80° C. in vacuum, reaction temperature is kept at 50-80° C. for 3 to 5 hours, controlling the quality of resulting products by dissolving into water and measuring the transparency, if it fails then continuing heating and measuring this transparency every 30 minutes until it is observed to be transparent, the reation is quenched, the temperature is decreased slowly until it is in the range of 40 to 60° C.

By theoretical and experimental studies, the inventors found that to produce nano-CBDs with good water solubility, the emulsion system will be in the form of oil-in-water emulsion. Selecting emulsifiers to enhance the durability of the microemulsion system was based on properties of this microemulsion system (in the form of oil-in-water microemulsion system, in the form of water-in-oil microemulsion system, etc.). Thus, the inventors selected ACRYSOL K-140 also known as PEG-40 hydrogenated castor oil, as an emulsifier, because ACRYSOL K-140 is a hydrophilic, non-toxic and highly safe agent. The inventors had to carry out so many studies to determine ratios of PEG:ACRYSOL K-140 to generate sustainable polymer chains. As the emulsifier ACRYSOL K-140 is a molecule with 2 distinct portions, an oleophylic portion and a hydrophylic portion, it is capable of forming linkages with CBDs and carrier mixtures. The oleophylic portion of ACRYSOL K-140 forms a linkage with the CBD and the hydrophylic portion of ACRYSOL K-140 forms a linkage with the hydrophylic portion of the mixture of PEG carriers then create nano-CBD micelles and protect CBD activity well with this structure. Generating a nano-CBD microemulsion system by simultaneously stirring at a speed of 400 to 600 rpm in vacuum, the reaction temperature is kept at100° C. for 3 to 5 hours, then emulsifying the entire mixture for 30 minutes, at a speed of 400 to 800 rpm.

The microemulsion system obtained by the process of the present invention has pH of 7-7.4. With these pH values, micelles exist stably as the linkage between the CBD and the carrier material is kept in dispersing process in this neutral environment, while the microemulsion system has pH<7 then this linkage weakens resulting the damage of nano-CBD particles in the digestive tract.

The nano-CBD microemulsion system obtained by the process of the present invention having HLB of 13-18 is a hydrophylic microemulsion system. The microemulsion system has micelles containing hydrophylic CBDs, are inadherent with particle sizes ranging stably from 30 to 80 nm, then it can easily penetrate via cell membranes to develop the effectiveness and increase the solubility of CBDs in water, thereby enhance the bioavailability of the agents.

(v) Fifth step: filtrating the products by injecting through nanofilters before filling-packaging to remove excessive amounts of agents and ensure the uniformity, the stability of solutions.

EXAMPLES

Example

Production of 100 ml of Nano-CBD Microemulsion System

A dispersal phase was prepared by dissolving 8 g of CBD in 10 ml of ethanol solvent 960 with a stirrer at a speed of 400 rpm, simultaneously heated to a temperature of 40° C. for 6 hours to form a homogeneous solution.

Producing a carrier: 70 ml of PEG was heated to 70° C. 70 ml of the carrier was added to the above-prepared dispersal phase, this dispersal phase continued to be heating to 100° C. and stirred at a speed of 600 rpm. A homogeneous mixture was prepared by mixing the dispersal phase, a mixture of PEG carrier and emulsifier ACRYSOL K-140 (20 ml) in an emulsifying equipment LSP –500 with a frequency of 20 KHz at a stirring speed of 600 rpm, at 80° C., continued to be stirring at a speed of 600 rpm, at the same time stirred at a speed of 500 rpm in vacuum, the reaction temperature was kept at 80° C. for 4 hours, the quality of resulting products was controlled by dissolving into water and the transparency was measured, if it failed then continuing heating and measuring this transparency every 30 minutes until it was observed to be transparent, the reation was quenched, the temperature was decreased slowly until it was 50° C.

Before filling, the products were injected via nanofilters for the purpose of removing the excessive amounts of CBDs which did not form micelles, gave a nano-CBD microemulsion system which dispersed in water well.

By UV-vis spectrophotometry methods, the inventors found that positions of peaks of material CBDs and the nano-CBD microemulsion system fitted completely. This showed that the microemulsion system obtained by the process of the present invention retained the structure, activity of CBDs in nanoprocessing. UV-vis spectrophotometry methods were used to quantify the concentrations of CBDs in the microemulsion system. The results showed that the concentrations of CBDs in the nano-CBD microemulsion system were in the range of about 10%.

Figure 2:
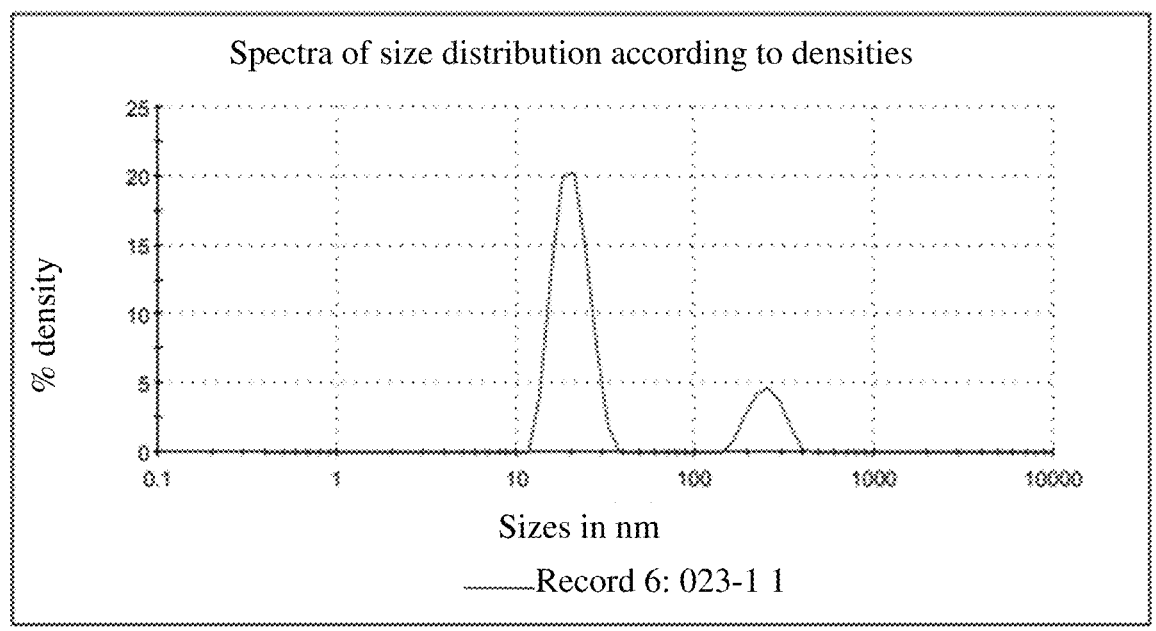
FIG. 2 shows a picture of spectra measuring by TEM the sizes of nano-CBD particles obtained by the process of the invention.

Measuring sizes of nano-CBD particles by a scanning electron microscope TEM (Transmission Electron Microscopy) shown in FIG. 2 demonstrated that particle sizes fluctuating from 20 to 85 nm accounted for 81.5% in solution.

Particle sizes measured by DLS: particles suspending in a fluid continued undergoing random motions, and the particle sizes directly affected on their speeds. Small particles moved faster than bigger ones. In DLS, lights went through samples, and scattering lights were detected and recorded in a certain angle.

Zeta potential or kinetic potential: the potential between a dispersal phase and a dispersing media.

| Sizes (nm, according to TEM) | Sizes (nm, according to DLS) | Zeta potential (mV) | Stability (months) | Water solubility |
|---|---|---|---|---|
| 30-80 | 30-80 | −40 | >12 | Well-water solubility, after solubilized in water, the system stabilized >7 days |

The above results showed that using PEG carriers with ACRYSOL K-140 gave a microemulsion system with micelles having small dimensions ranging from 20 to 85 nm, high stability (>12 months), well-water solubility and after dissolved in water, the system stabilized >7 days.

With the reference to FIG. 1, it shows a picture comparing the water-dispersing ability between a known 99% CBD and the nano-CBD obtained by the process of the present invention, in which bottle A showed the known 99% water-dispersed CBD, bottle B showed the water-dispersed nano-CBD obtained by the process of the present invention. FIG. 1 showed that the known 99% CBD was insoluble in water, formed water-suspending particles, a cloudy solution which encrusted at the bottom of bottle (A) over time; the nano-CBD obtained by the process of the present invention completely dispersed in water generated a transparent, homogeneous solution (B)

With the reference to FIG. 2 showing the results of picture of spectra measuring by TEM the sizes of nano-CBD particles obtained by the process the present invention, it was found that the average particle size was 27.25 nm, with the density of 81.5%, spectrum peak 1 having the particle diameter of 20.61 nm, the width of 4.376 nm. Particles had the uniformity of sizes fluctuating from about 20 to 85 nm (FIG. 2), appeared spectrum peaks 2 having the particle diameter of 250.5 nm, the width of 51.17 nm but accounted for only 18.5%.

Table below shows measurement data:

|  |  | Diameter (nm) | % density | Width (nm) |
|---|---|---|---|---|
| The average particle size (d · nm): 27.25 | Spectrum peak 1 | 20.61 | 81.5 | 4.376 |
| Pdl: 0.412 | Spectrum peak 2 | 250.5 | 18.5 | 51.17 |
| Blocking ability: 0.930 | Spectrum peak 3 | 0.00 | 0.00 | 0.00 |
| Result of evaluation: Good | | | | |

Advantageous Effects of Invention

The process for producing a nano-CBD microemulsion system of the present invention succeeds in manufacturing a microemulsion system having nano-CBD micelles with small dimensions of about 20 to 85 nm, which is uniform and good water-soluble while retains the structure, activity of CBDs in nanoprocessing.

The agents used in the process for producing nano-CBD, which disperse well in water, are highly safe, non-toxic and have less side effects, then the nano-CBD microemulsion system obtained by the process of the present invention has high safety when being used.

The process of the present invention is simple, easy to perform and suitable with current actual conditions in our country.

The invention claimed is:

1. A process for producing a nano-Cannabidiol (CBD) microemulsion system includes:
   (i) preparing a dispersal phase by dissolving CBD in an ethanol solvent in a ratio between mass of CBD: volume of ethanol solvent as 8:10 with a stirrer at a speed of 300 to 500 rpm with heating to a temperature ranging from 40 to 60° C. within 4 to 8 hours;
   (ii) preparing a carrier by heating a liquid PEG (polyethylene glycol) accounted for 40-60% by mass of the mixture of PEG and water to a temperature from 60 to 80° C., stirring homogeneously;
   (iii) adding the carrier to the dispersal phase in a ratio by mass of 40:60, continuing heating this dispersal phase to 100° C. stirring at a speed of 400 to 800 rpm;
   (iv) emulsifying as follows: when the temperature arrives at 100° C., PEG-40 hydrogenated castor oil to the mixture of carrier and dispersal phase in step (iii) in a ratio by mass of 40:60, continuing to stir at a speed of 500 to 700 rpm, at a
   reaction temperature of about 100° C., in a vacuum, the reaction temperature is kept at 100° C. for 3 to 5 hours, and the resulting mixture is heated every 30 minutes until a transparent mixture is observed, when the transparent mixture is observed the reaction is quenched by slowly decreasing the temperature until it is in the range of 40° C. to 60° C.; then emulsifying the entire mixture for 30 minutes, at a speed of 400 to 800 rpm
   (v) filtrating the products by injecting via nanofilters and then filling-packaging.

* * * * *